United States Patent
Koncar et al.

(10) Patent No.: US 6,696,583 B2
(45) Date of Patent: Feb. 24, 2004

(54) METHOD FOR PREPARING FATTY ACID ALKYL ESTERS

(75) Inventors: Michael Koncar, Teichstrasse 9, Lieboch (AT), A-8501; Martin Mittelbach, Am Blumenhang 27, Graz (AT), A-8010; Helmut Gössler, Mooskirchen (AT); Wilhelm Hammer, Graz (AT)

(73) Assignees: Michael Koncar, Lieboch (AT); Martin Mittelbach, Graz (AT); BDI Anlagenbau Gesellschaft mbH, Feldkirchen (AT)

( * ) Notice: Subject to any disclaimer, the term of this patent is extended or adjusted under 35 U.S.C. 154(b) by 0 days.

(21) Appl. No.: 10/161,761

(22) Filed: Jun. 4, 2002

(65) Prior Publication Data

US 2003/0004363 A1 Jan. 2, 2003

Related U.S. Application Data

(63) Continuation of application No. PCT/AT01/00320, filed on Oct. 5, 2001.

(30) Foreign Application Priority Data

Oct. 5, 2000 (AT) .......................................... 1699/2000

(51) Int. Cl.$^7$ ................................................ C11C 3/10
(52) U.S. Cl. ..................................................... 554/169
(58) Field of Search .......................................... 554/169

(56) References Cited

U.S. PATENT DOCUMENTS 5,424,466 A    6/1995  Stern et al.
5,849,939 A  * 12/1998  Mittelbach et al. ......... 554/169

FOREIGN PATENT DOCUMENTS

WO           WO9502661      1/1995

OTHER PUBLICATIONS

Lago et al., 1985, "Extraction and transesterification of vegetable oils with ethanol," Oleagineux 40:147–15.

* cited by examiner

Primary Examiner—Deborah D. Carr
(74) Attorney, Agent, or Firm—Baker Botts LLP

(57) ABSTRACT

A method for the preparation of fatty acid alkyl esters by transesterification, in particular catalytic transesterification, of a mixture of triglycerides and fatty acids, wherein from a reaction mixture, in which the transesterification is carried out, an ester phase containing fatty acid alkyl esters and a glycerol phase containing fatty acids are formed, which are separated from each other, and the fatty acids are separated from the glycerol phase, whereby a fatty acid phase containing fatty acids is formed, which fatty acids are esterified with an alcohol, which method is characterized in that the fatty acid phase is mixed with a further mixture of triglycerides and fatty acids and the fatty acids contained in the obtained mixture are esterified with an alcohol, whereby an esterification mixture containing triglycerides and fatty acid alkyl esters is obtained, which esterification mixture is transesterified with alcohol so as to form further fatty acid alkyl esters.

31 Claims, No Drawings

METHOD FOR PREPARING FATTY ACID ALKYL ESTERS

CROSS REFERENCE TO RELATED APPLICATIONS

This application is a continuation of copending International Patent Application No. PCT/AT01/00320 filed Oct. 5, 2001, which claims priority to Austrian Patent Application No. A1699/2000 filed Oct. 5, 2000.

STATEMENT REGARDING FEDERALLY SPONSORED RESEARCH

Not applicable.

REFERENCE TO SEQUENCE LISTING

Not Applicable.

BACKGROUND OF THE INVENTION

1. Field of the Invention

The invention relates to a method for the preparation of fatty acid alkyl esters by transesterification, in particular catalytic transesterification, of a mixture of triglycerides and fatty acids, wherein from a reaction mixture, in which the transesterification is carried out, an ester phase containing fatty acid alkyl esters and a glycerol phase containing fatty acids are formed, which are separated from each other, and the fatty acids are separated from the glycerol phase, whereby a fatty acid phase containing fatty acids is formed, which fatty acids are esterified with an alcohol.

By triglycerides, esters formed from saturated and/or unsaturated higher fatty acids and glycerol are to be understood for the purpose of the present specification and patent claims. Such esters are, for example, fats originating from plant or animal sources and also spent edible oils and waste fats. However, many fats coming from natural sources also contain free fatty acids to a more or less large extent. Those fats thus are a mixture of triglycerides and free fatty acids, the main component of that mixture generally being the triglycerides.

By transesterification, the alcoholysis of triglycerides is to be understood, i.e. the reaction with alcohols, in particular methanol and ethanol, wherein the monoesters of the fatty acids as well as glycerol are formed via the intermediate products di- and monoglycerides.

2. Description of Related Art

Fatty acid esters, in particular the methyl esters, are important intermediate products in oleochemistry. In Europe alone, 200,000 tons of vegetable oil methyl ester are produced annually as raw materials primarily for surfactants. Beside this, the fatty acid methyl ester is of increasing importance as a substitute for diesel fuel.

As the catalysts for the transesterification, basic catalysts (alkali hydroxides, alcoholates, oxides, carbonates, anion exchangers), acidic catalysts (mineral acids, p-toluene sulfonic acid, boron trifluoride, cation exchangers) and enzymes (lipases) may be used. Today catalysts which are soluble in the reaction mixture are preferably used. They form a homogeneous mixture and guarantee fast reaction rates and mild reaction conditions. The homogeneous catalysts most frequently used are sodium and potassium hydroxide as well as sodium methylate, which, dissolved in alcohol, are admixed to the vegetable oil. Such a method is known from AT-B 386222. The acidic catalysis requires higher reaction temperatures and pressures and a more complex reaction procedure. An acidic transesterification is known from FR-A-85 02340.

Transesterification with basic catalysis is carried out without the use of a solvent. The reaction starts with a two-phase system of triglyceride and alcohol; yet during reaction progress and the formation of ester, a homogeneous phase forms, which turns into two phases again by the formation and separation of glycerol.

In the alcoholysis of triglycerides for the preparation of esters of the fatty acids with monohydric alcohols, a phase rich in glycerol is produced as a by-product. This phase further contains fatty acids, fatty acid salts and fatty acid esters. In order to separate these fatty acid compounds from the glycerol phase, it is generally treated with acids. By this treatment, the fatty acids are set free from the fatty acid salts. The fatty acids as well as the fatty acid esters themselves are not miscible with glycerol and therefore settle as a separate phase from the glycerol phase. This phase is referred to as fatty acid phase.

A method of the initially mentioned kind can be gathered from EP-A- 0 708 813. That previously known method utilizes the fatty acid phase by esterifying the fatty acids contained in that phase with an alcohol and by adding the obtained fatty acid alkyl esters to another reaction mixture, in which transesterification is just being carried out.

As already mentioned, fats coming from natural sources also contain free fatty acids to varying extents. The higher that content of free fatty acids is, the less triglyceride is available as a raw material for transesterification. On the other hand, the yield of fatty acid alkyl esters may be increased if the free fatty acids are esterified in a separate step as it is the case in the above mentioned EP-A- 0 708 813.

From Oleagineux, vol. 40, no. 3, pp. 148–151 (1985), it is known to esterify the free fatty acids contained in the fatty acid phase to the ethyl ester by means of ethanol-containing miscella while sulphuric acid is used as a catalyst, to neutralize the sulphuric acid with CaO, to filter off the calcium sulfate formed, to mix the obtained ester with a transesterification catalyst and to trans esterify a miscella rich in oil with this mixture. Miscella is obtained during the extraction of the raw material containing oil or fat, respectively, and thus is a mixture of an extracting agent and triglyceride to be transesterified. That method is very costly and is not very suitable for the transesterification of oil-containing raw materials which contain free fatty acids.

BRIEF SUMMARY OF THE INVENTION

This is where the present invention sets in and it is its object to provide a method of the initially decribed kind according to which the fatty acid phase may be processed in the untreated state, i.e. without purification and removal of sulphuric acid, and according to which also raw materials having a larger content of free fatty acids may be transesterified.

BRIEF DESCRIPTION OF THE DRAWINGS

Not applicable.

DETAILED DESCRIPTION OF THE INVENTION

The method according to the invention is characterized in that the fatty acid phase is mixed with a further mixture of triglycerides and fatty acids and the fatty acids contained in the obtained mixture are esterified with an alcohol, whereby an esterification mixture containing triglycerides and fatty acid alkyl esters is obtained, which esterification mixture is transesterified with alcohol so as to form further fatty acid alkyl esters.

According to the method of the invention, thus the fatty acids contained in the fat or oil, respectively, to be transesterified (i.e. a mixture of triglycerides and fatty acids) are esterified with an alcohol prior to the actual transesterification, whereby that esterification is carried out in the presence of the fatty acid phase from a previous transesterification, so that both the fatty acids contained in the fat to be transesterified and the fatty acids contained in the admixed fatty acid phase are esterified.

The fatty acid phase from the previous transesterification does not need to be purified and may be added to the fat as such, i.e. plus the excess methanol.

If the fat contains a very large content of free fatty acids, the esterification mixture obtained after a first esterification may be esterified with alcohol for at least another time prior to the transesterification. In this manner, the content of free fatty acids may be gradually decreased so that a yield of fatty acid alkyl esters of 100% becomes possible.

Thus, a preferred embodiment of the method of the invention is characterized in that the mixture of triglycerides and fatty acids mixed with the fatty acid phase exhibits a fatty acid content of at least 5% by weight, in particular of at least 10% by weight.

Preferably, the esterification is carried out under acidic catalysis and, preferably, the transesterification is carried out under alkaline catalysis.

In the method according to the invention, in particular methanol or ethanol is employed as an alcohol for the transesterification and the esterification.

An exemplary embodiment of the invention is described in more detail by way of the following example.

EXAMPLE

1. Esterification

First, 1.000 g of spent edible oil having a content of free fatty acids of 7.15% was mixed with 100 g of methanol and 7.0 g of H2SO4 (98%) for esterification and was refluxed for 2 hours. The batch was transferred into a separating funnel and was separated into an aqueous phase (51.6 g) and an oil phase (1,045.0 g).

2. Transesterification

The oil phase was subjected to a two-stage, alkaline transesterification in accordance with the method described in AT-B 386.222. By doing so, the oil phase was mixed with altogether 192.2 g of methanol and 12.19 g of KOH, and the glycerol phase formed was separated after each stage. The ester phase formed (917.8 g) was demethanolized in a Rotavapor (40.8 g) so that 877.0 g of fatty acid methyl ester was obtained.

3. Formation of the fatty acid phase

By adding 12.0 g of H2SO4, the two glycerol phases (328.1 g) recovered from transesterification were brought to a pH value of approximately 3. By that acidification, free fatty acids and potassium salt provided as a solid phase were formed from the potassium soaps existing in the glycerol phase. The mixture formed was filtered, and the filtrate was transferred into a separating funnel. After the phase separation, the amounts were as follows: fatty acid phase 103.5 g, glycerol phase 200.2 g, filtration residue 32.8 g.

4. Esterification

The fatty acid phase thus recovered (103.5 g) was mixed with 896.5 g of spent edible oil having a content of free fatty acid of 7.15% and, for esterification, was refluxed with 100 g of methanol and 7.0 g of H2SO4 (98%) for 2 hours. The batch was transferred into a separating funnel and was separated into an aqueous phase (59.2 g) and an oil phase (1,047.8 g). The content of free fatty acids in the oil amounted to 0.98%.

5. Transesterification

The oil phase was again subjected to a two-stage, alkaline trans esterification in accordance with AT-B 386.222. By doing so, the oil phase was mixed with altogether 190.8 g of methanol and 12.11 g of KOH, and the glycerol phase formed was separated after each stage. The ester phase formed (1,016.4 g) was demethanolized in a Rotavapor (56.3 g), whereby 907.1 g remained as a pure ester phase.

6. Formation of the fatty acid phase

The glycerol phases from transesterification (282.1 g) were joined together and brought to a pH value of approximately 3 by adding 10.1 g of H2SO4. The mixture formed was filtered, and the filtrate was transferred into a separating funnel. After the phase separation, the amounts were as follows: fatty acid phase 97.2 g, glycerol phase 161.2 g, filtration residue 33.8 g.

The obtained fatty acid phase may again be mixed with spent edible oil and may be used for the further manufacture of methyl ester.

What is claimed is:

1. A method for the preparation of fatty acid alkyl esters by transesterification, comprising the steps of:
 (i) performing a transesterification reaction wherein an ester phase, comprising fatty acid alkyl esters, and a glycerol phase, comprising fatty acids, are formed;
 (ii) collecting the glycerol phase formed in step (i);
 (iii) treating the glycerol phase collected in step (ii) to form a fatty acid phase comprising fatty acids;
 (iv) combining the fatty acid phase of step (iii) with triglycerides and fatty acids to form a mixture;
 (v) esterifying fatty acids in the mixture formed in (iv) with an alcohol to form an esterification mixture comprising triglycerides and fatty acid alkyl esters; and
 (iv) transesterifying the esterification mixture formed in (v) with an alcohol to form further fatty acid alkyl esters.

2. The method of claim 1, wherein the esterification mixture formed in step (v) additionally comprises residual fatty acids, comprising a further step of esterifying residual fatty acids in the esterification mixture with an alcohol prior to transesterification by step (vi).

3. The method according to claim 2 wherein the triglycerides and fatty acids mixed with the fatty acid phase exhibits a fatty acid content of at least five percent by weight.

4. The method according to claim 2 wherein the triglycerides and fatty acids mixed with the fatty acid phase exhibits a fatty acid content of at least five percent by weight.

5. The method according to claim 3 wherein the triglycerides and fatty acids mixed with the fatty acid phase exhibits a fatty acid content of at least ten percent by weight.

6. The method according to claim 4 wherein the triglycerides and fatty acids mixed with the fatty acid phase exhibits a fatty acid content of at least ten percent by weight.

7. The method according to claim 1, wherein the esterification is carried out under acidic catalysis.

8. The method according to claim 2, wherein the esterification is carried out under acidic catalysis.

9. The method according to claim 3, wherein the esterification is carried out under acidic catalysis.

10. The method according to claim 4, wherein the esterification is carried out under acidic catalysis.

11. The method according to claim 5, wherein the esterification is carried out under acidic catalysis.

12. The method according to claim 6, wherein the esterification is carried out under acidic catalysis.

13. The method according to claim 1, wherein the transesterification is carried out under alkaline catalysis.

14. The method according to claim 2, wherein the transesterification is carried out under alkaline catalysis.

15. The method according to claim 3, wherein the transesterification is carried out under alkaline catalysis.

16. The method according to claim 4, wherein the transesterification is carried out under alkaline catalysis.

17. The method according to claim 5, wherein the transesterification is carried out under alkaline catalysis.

18. The method according to claim 6, wherein the transesterification is carried out under alkaline catalysis.

19. The method according to claim 7, wherein the transesterification is carried out under alkaline catalysis.

20. The method according to claim 8, wherein the transesterification is carried out under alkaline catalysis.

21. The method according to claim 9, wherein the transesterification is carried out under alkaline catalysis.

22. The method according to claim 10, wherein the transesterification is carried out under alkaline catalysis.

23. The method according to claim 11, wherein the transesterification is carried out under alkaline catalysis.

24. The method according to claim 12, wherein the transesterification is carried out under alkaline catalysis.

25. The method according to claim 1, wherein the alcohol used for esterification and transesterification is selected from the group consisting of methanol and ethanol.

26. The method according to claim 2, wherein the alcohol used for esterification and transesterification is selected from the group consisting of methanol and ethanol.

27. The method according to claim 3, wherein the alcohol used for esterification and transesterification is selected from the group consisting of methanol and ethanol.

28. The method according to claim 7, wherein the alcohol used for esterification and transesterification is selected from the group consisting of methanol and ethanol.

29. The method according to claim 13, wherein the alcohol used for esterification and transesterification is selected from the group consisting of methanol and ethanol.

30. A method for the preparation of fatty acid alkyl esters by transesterification, comprising the steps of:
(i) performing a transesterification reaction wherein an ester phase, comprising fatty acid alkyl esters, and a glycerol phase, comprising fatty acids, are formed;
(ii) collecting the glycerol phase formed in step (i);
(iii) treating the glycerol phase collected in step (ii) to form a fatty acid phase comprising fatty acids which are esterified by an alcohol;
(iv) combining the fatty acid phase of step (iii) with triglycerides and fatty acids to form a mixture;
(v) esterifying fatty acids in the mixture formed in (iv) with an alcohol to form an esterification mixture comprising triglycerides and fatty acid alkyl esters; and
(iv) transesterifying the esterification mixture formed in (v) with an alcohol to form further fatty acid alkyl esters.

31. A method for the preparation of fatty acid alkyl esters by transesterification, comprising the steps of:
(i) performing a transesterification reaction wherein an ester phase, comprising fatty acid alkyl esters, and a glycerol phase, comprising fatty acids, are formed;
(ii) collecting the glycerol phase formed in step (i);
(iii) treating the glycerol phase collected in step (ii) to form a fatty acid phase comprising fatty acids;
(iv) combining the fatty acid phase of step (iii) with triglycerides and fatty acids to form a mixture;
(v) esterifying fatty acids in the mixture formed in (iv) with an alcohol to form an esterification mixture comprising triglycerides and fatty acid alkyl esters;
(vi) transesterifying the esterification mixture formed in (v) with an alcohol to form further fatty acid alkyl esters and a glycerol phase; and
(vii) collecting the glycerol phase formed in step (vi) and repeating steps (iii)–(vi) to form additional fatty acid alkyl esters.

* * * * *